US008722088B2

(12) United States Patent
Olesen et al.

(10) Patent No.: US 8,722,088 B2
(45) Date of Patent: May 13, 2014

(54) PHARMACEUTICAL COMPOSITIONS AND METHODS FOR THE TREATMENT OF PROSTATE CANCER

(75) Inventors: Tine Kold Olesen, New York, NY (US); Lars Erichsen, Farum (DK); Per Cantor, Charlottenlund (DK)

(73) Assignee: Ferring International Center S.A., Saint-Prex (CH)

( * ) Notice: Subject to any disclaimer, the term of this patent is extended or adjusted under 35 U.S.C. 154(b) by 417 days.

(21) Appl. No.: 12/771,199

(22) Filed: Apr. 30, 2010

(65) Prior Publication Data

US 2010/0305042 A1    Dec. 2, 2010

Related U.S. Application Data

(60) Provisional application No. 61/187,819, filed on Jun. 17, 2009.

(30) Foreign Application Priority Data

May 1, 2009    (EP) .................................... 09251242

(51) Int. Cl.
*A61K 9/22* (2006.01)
*A61K 38/22* (2006.01)
*A61K 38/24* (2006.01)

(52) U.S. Cl.
USPC ........... 424/468; 514/9.7; 514/10.1; 514/10.3

(58) Field of Classification Search
None
See application file for complete search history.

(56) References Cited

U.S. PATENT DOCUMENTS

| | | | |
|---|---|---|---|
| 3,773,919 | A | 11/1973 | Boswell |
| 5,506,207 | A | 4/1996 | Rivier et al. |
| 5,516,887 | A | 5/1996 | Deghenghi |
| 5,595,760 | A | 1/1997 | Cherif-Cheikh |
| 5,821,230 | A | 10/1998 | Jiang et al. |
| 5,860,957 | A | 1/1999 | Jacobsen et al. |
| 5,863,549 | A | 1/1999 | Taratino |
| 5,925,730 | A | 7/1999 | Semple et al. |
| 6,214,798 | B1 | 4/2001 | Semple et al. |
| 6,503,534 | B1 | 1/2003 | Pellet et al. |
| 7,884,071 | B2 * | 2/2011 | Bauer et al. ..................... 514/9.7 |
| 2003/0044463 | A1 * | 3/2003 | Deghenghi et al. ............ 424/468 |
| 2004/0038903 | A1 | 2/2004 | Luck et al. |
| 2004/0138610 | A1 | 7/2004 | Cormier et al. |
| 2005/0245455 | A1 | 11/2005 | Luck et al. |
| 2006/0135405 | A1 | 6/2006 | Rischer et al. |
| 2008/0032935 | A1 | 2/2008 | Engel et al. |
| 2009/0018085 | A1 | 1/2009 | Luck et al. |
| 2009/0203622 | A1 | 8/2009 | Persson |
| 2009/0209939 | A1 | 8/2009 | Verespej et al. |
| 2010/0286603 | A1 | 11/2010 | Winderstrom |
| 2010/0305042 | A1 | 12/2010 | Olesen et al. |
| 2011/0039787 | A1 | 2/2011 | Petri et al. |
| 2011/0053846 | A1 | 3/2011 | Luck et al. |
| 2012/0172302 | A1 | 7/2012 | Petri et al. |
| 2013/0018223 | A1 | 1/2013 | Joseph |
| 2013/0029910 | A1 | 1/2013 | Meulen et al. |
| 2013/0281661 | A1 | 10/2013 | Rasmusse et al. |
| 2013/0281662 | A1 | 10/2013 | Kalita et al. |
| 2013/0295166 | A1 | 11/2013 | Grenier et al. |

FOREIGN PATENT DOCUMENTS

| | | |
|---|---|---|
| CN | 1411803 A | 4/2003 |
| EP | 0 002 749 B1 | 10/1983 |
| EP | 0 556 034 A1 | 8/1993 |
| EP | 1 003 774 B1 | 5/2000 |
| EP | 1 967 202 A1 | 9/2008 |
| FR | 2 776 520 A | 10/1999 |
| WO | WO03/006049 A1 | 10/2003 |
| WO | WO 2004/080413 A2 | 9/2004 |
| WO | WO 2007/130809 A2 | 11/2007 |
| WO | WO 2008/135989 A1 | 11/2008 |
| WO | WO 2009/101533 A1 | 8/2009 |
| WO | WO 2011/004260 A2 | 1/2011 |

OTHER PUBLICATIONS van Poppel et al., European Urology; 54 (2008) pp. 805-815. Oringially published online ahead of print on May 8, 2008.*
Broqua et al., J. Pharmacology and Experimental Therapeutics (JPET); 301:95-102; 2002.*
The K-Zone, Biophysical data tables: standard man, Jul. 2004; printed Mar. 14, 2009 from www.kevinboone.com/biodat_stdman.html; 1 page.*
U.S. Patent Documents—none.*
Non-Patent Documents—none.*
"Alkaline Phosphatase," GP Notebook (Sep. 12, 2011), http://gpnotebook.co.uk/simplepage.cfm?ID=-1932525548.
Agerso, et al., "The dosing solution influence on the pharmacokinetic of degarelix, a new GnRH0 antagonist, after s.c. administration to beagle dogs," European Journal of Pharmaceutical Sciences, vol. 20, pp. 335-340, 2003.
Albertsen et al.., Reduced Risk Cardiovascular (CV) Events and Death in Patients (PTS) Receiving Degarelix Compared with LHRH Agonists (2012) Abstract.
Behn, et al., "The obesity epidemic and its cardiovascular consequences," (2006) Curr. Opin. Cardiol. vol. 21, pp. 353-360.
Berges, et al., "Effect of a new leuprorelin formulation on testosterone levels in patients with advanced prostate cancer," (2006), Cur. Med. Res. Opin., vol. 22, No. 4, pp. 649-655.
Boccon-Gibod, et al., "Cyproterone Acetate Lead-In Prevents Initial Rise of Serum Testosterone Induced by Luteinizing Hormone-Releasing Hormone Analogs in the Treatment of Mestastatic Carcinoma of the Prostate," (1986) Euro. Urol.,vol. 12, pp. 400-402.
'Bone Specific Alkaline Phosphatase,' The University of Iowa (UIHC), Department of Pathology, Laboratory Services Handbook (Sep. 11. 2011), http://www.healthcare.uiowa.edu/path_handbook/handbook/test2238.html.

(Continued)

*Primary Examiner* — Robert A Wax
*Assistant Examiner* — Jeffrey T Palenik
(74) *Attorney, Agent, or Firm* — Finnegan, Henderson, Farabow, Garrett & Dunner LLP (57) ABSTRACT

Compositions, kits, and methods are provided directed to the treatment of prostate cancer using a maintenance dose of degarelix or pharmaceutically acceptable salt thereof, an excipient, and a solvent.

35 Claims, 2 Drawing Sheets

(56) References Cited

OTHER PUBLICATIONS

Broqua et al., "Effects of the New GNRH Antagonist FE200486 one the Growth of the Adrogen-Dependent Prostate Tumor Dunning R-3327H, 6th International Symposium on GnRH Analogues in Cancer and Human Reproduction," Geneva, Switzerland,Feb. 8, 2001.
Broqua, et al., "Pharmacological Profile of a New, Potent, and Long-Acting Gonadotropin-Releasing Hormone Antagonist: Degarelix," The Journal of Pharmacology and Experimental Therapeutics, vol. 301, pp. 95-102, 2002.
Cancer Trends Progress Report, http://progressreport.cancer.gov.
Cetrotide TM package insert (Aug. 11, 2000).
Chernecky, and Berger, "Laboratory Tests and Diagnostic Procedures," (2008) Fifth Edition, WB Saunders & Company, Philadelphia. ISBN-978-1-14160-3704-0.
Co-pending U.S. Appl. No. 12/368,713.
Co-pending U.S. Appl. No. 12/368,935.
Co-pending U.S. Appl. No. 12/771,199.
Co-pending U.S. Appl. No, 12/774,113.
Co-pending U.S. Appl. No. 12/829,467.
Co-pending U.S. Appl. No. 12/901,270.
Co-pending U.S. Appl. No. 12/155,897, filed Jun. 11, 2008.
Crawford et al., "A Phase III Extension Trial With a 1-Arm Crossover From Leuprolide to Degarelix: Comparison of Gonadotropin-Releasing Hormone Agonist and Antagonist Effect of Prostate Cancer," 186 The Journal of Urology 889-897 (2011).
de la Rosette et al., "Efficacy and safety of androgen deprivation therapy after switching from monthly leuprolide to monthly degarelix in patients with prostate cancer," 65(5) International Journal of Clinical Practice 559-66 (2011).
de Pinieux, et al., "Clinical and Experimental Progression of a New Model of Human Prostate Cancer and Therapeutic Approach," American Journal of Pathology, vol. 159, No. 2, Aug. 2001.
Debruyne, et al., "Abarelix for injectable suspension: first-in-class gonadotropin-releasing hormone antagonist for prostate cancer," (2006) Future Oncol., vol. 2, pp. 677-696.
Demers et al., "Biochemical Markers and Skeletal Metastases," Cancer, vol. 88, pp. 2919-2926, Mar. 2, 2000.
Denis, et al., "Overview of Phase III Trials on Combined Androgen Treatment in Patients with Metastatic Prostate Cancer," (1993) Cancer, vol. 72, pp. 3888-3895.
Eastman et al., "Serum Alkaline Phosphatase: Normal Values by Sex and Age," 23 (9) Clinical Chemistry 1769-1770 (1977).
Etzioni, et al., "Cancer Surveillance Series: Interpreting Trends in Prostate Cancer—Part III: Quantifying the Link Between Population Prostate-Specific Antigen Testing and Recent Declines in Prostate Cancer Mortality," (1999) J. Natl. Canc. Inst., vol. 91, pp. 1033-1039.
European Seach Report & Opinion, dated Oct. 2, 2012, EP Application No. 12168495.5.
FDA Drug Information Page—Plenaxis (abarelix for injectable suspension); http://www.fda.gov/cder/drug/infopage/planaxis/default.htm.
Ferlay,et al., "Estimates of the cancer incidence and mortality in Europe in 2006," Annals of Oncology, vol. 18, pp. 581-592 (2007).
Fleming,et al., "Post-therapy changes in PSA as an outcome measure in prostate cancer clinical Trials," (2006) Nature Clinical Practice Oncolology, vol. 3, No. 12, pp. 658-667.
Forbes, et al., "FDA'S Adverse Drug Reaction Drug Dictionary and Its Role in Post-Marketing Surveillance," (1986) Drug Inf. J., vol. 20, pp. 135-145.
Gerlinger, et al.,"Recommendation for Confidence interval and sample size calculations for the Pearl Index," (2003) The European Journal of Contraception and Reproductive Health Care, vol. 8, pp. 87-92.
Gillum Lu, T., "The Merck Regulatory Dictionary: A Pragmatically Develop Drug Effects Vocabulary," (1989) Drug Info. J., vol. 23, pp. 217-220.
Gittelman et al., "A 1-Year, Open Label, Randomized Phase II Doe Finding Study of Degarelix for the Treatment of Prostate Cancer in North America," The Journal of Urology, vol. 80, pp. 1986-1992, Nov. 2008.

Granfors, et al., "Combined Orchiectomy and External Radiotherapy Versus Radiotherapy Alone for Nonmetastatic Prostate Cancer With or Without Pelvic Lymph Node Involvement: A Prospective Randomized Study," J. Urol., (1998), 159:2030-34.
Hackman, et al., "Emerging Risk Factors for Atherosierotic Vascular Disease," (2003), JAMA, vol. 290, pp. 932-940.
Hegele et al., "Biochemical Markers of Bone Turnover in Patients with Localized and Metastasized Prostate Cancer," Journal Compilation, vol. 99, pp. 330-334. Sep. 7, 2006.
Hellerstedt, et al., "The Current State of Hormonal Therapy for Prostate Cancer," CA A Cancer Journal for Clinicians, vol. 52, pp. 154-179.
International Search Report issued on Sep. 12, 2002, in Application No. PCT/GB02/03116.
Jiang et al., "Betidamino Acid-Scan of the GNRH Antagonist Acyline," Journal of Medicinal Chemistry, American Chemical Socitey, Washington, US, vol. 40, 1997, pp. 3739-3748.
Jiang, et al.,"GnRH Antagonists: A New Generation of Long Acting Analogues Incorporating p-Ureido-phenylalanies at Positions 5 and 6," (2001) J. Med. Chem., vol. 44, pp. 453-467.
Kirk et al., "Immediate Versus deferred treatment for advanced prostatic cancer; initial results of the Medical Research Counsel trial.," British Journal of Urology, (1997) vol. 79, pp, 235-246.
Lehmann, "Testing Statistical Hypotheses," (1986) Second Edition, John Wiley & Sons New York ISBN 0-471-84083-1.
Lilja, et al., "Prostate-specific antigen and prostate cancer: prediction, detection and monitoring," (2008) Nature Reviews/Cancer, vol. 8, pp. 268-278.
Lukka, et al., "Maximal androgen blockade for the treatment of metastatic prostate cancer—a systematic review," Current Oncology, vol. 13, No. 3, pp. 81-93.
Lyseng-Williamson, Katherine A., "Degarelix: a guide to its use in advanced prostate cancer," 28(5) Drugs Ther. Perspect. 6-10 (2012).
McNeil, et al., "On the Elicitation of Preferences for Alternative Therapies," (1982) N. Engl. J. Med., vol. 306, No. 21, pp. 1259-1262.
Messing, et al., "Immediate Hormonal Therapy Compared with Observation after Radical Prostatectomy and Pelvic Lyphadenectomy in Men with Node-Positive Prostate Cancer," (1999), N. Eng, J. Med., vol. 341, pp. 1781-1788.
Miller et al., Differential outcomes from an analysis of six comparative randomised clinical trials of degarelix versus luteinising hormone-releasing hormone (LHRH) agonists) (2012).
Miller et al., "Disease control-related outcomes from an analysis of six comparative randomised clinical trials of degarelix versus luteinising hormone-releasing hormone (LHRH) agonists," (2012).
Mongiat-Artus, et al., "Abarelix: the first gonadotrophin-releasing hormone antagonist for the treatment of prostate cancer," (2004), Expert Opin. Pharmacother, vol. 5, pp. 2171-2179.
Office Action mailed Apr. 2, 2012, in copending U.S. Appl. No. 12/368,935.
Office Action mailed Jan. 31, 2013, in copending U.S. Appl. No. 12/901,270.
Office Action mailed Mar. 1, 2011, in copending U.S. Appl. No. 12/368,713.
Office Action mailed Mar. 8, 2011, in copending U.S. Appl. No. 12/155,897.
Office Action mailed Oct. 12, 2011, in U.S. Appl. No. 12/155,897.
Office Action mailed Oct. 22, 2009, in co-pending U.S. Appl. No. 12/155,897.
Persad, "Leuprorelin Acetate in Prostate Cancer: A European Update," (2002) Int. J. Clin. Pract., vol. 56, No. 5, pp. 389-396.
Romero-Corral, et al., "Association of bodyweight with total mortality and with cardiovascular events in coronary artery disease: a systematic review of cohort studies," (2006) Lancet, 368:666-678.
Saltzman, A., "Adverse Reaction Terminology Standardization: A Report on Schering-Plough's Use of the WHO Dictionary and the Formation of the WHO Adverse Reaction Terminology Users Group (WUG) Consortium," (1985) Drug Info. J., vol. 19, pp. 35-41.
Smith et al., "Cardiovascular Safety of Degarelix: Results From a 12-Month, Comparative, Randomized, Open Label, Parallel Group Phase III Trial in Patients With Prostate Cancer," 184 The Journal of Urology 2313-2319 (2010).

(56) References Cited

OTHER PUBLICATIONS

Smith, M.R. et al., "Gonadotropin-Releasing Hormone Blockers and Cardiovascular Disease Risk: Analysis of Prospective Clinical Trials of Degarelix," 186 The Journal of Urology 1835-1842 (2011).
Sorbera et al., "Degarelix Acetate", GnRH Antagonist Prostate Cancer Therapy; Drugs of the Future 2006, vol. 31, No. 9, pp. 755-766.
Spilker, Bert, "Guide to Cinical Trials," (1991) Raven Press, Ltd., New York, ISBN 0-88167-767-1.
Spilker, Bert, "Quality of Life and Pharmacoeconomics in Clinical Trials," (1996) Lippincott—Raven Publishers, New York, ISBN 0-7817-0332-8.
Steinberg, et al., "Degarelix: A Gonadotropin-Releasing Hormone Antagonist for the Management of Prostate Cancer," Clinical Therapeutics, vol. 31, pp. 2312-2331, 2009.
Stephens, M.D.B., "The Detection of New Adverse Drug Reactions," (1988) Stockton Press, New York, ISBN 0-333-45417-0.
Teal, et al., "Adverse Drug Experience Management: A Brief Review of the McNeil Pharmaceutical System," (1985) Drug Info. J., vol. 19, pp. 17-25.
Thompson, et al., "Sudden Death to Disease Flare With Luteinizing Hormone-Releasing Hormone Agonist Therapy for Carcinoma of the Prostate," J. Urol., (1990) vol. 144, pp. 1479-1480.
Turner, et al., "The Processing of Adverse Reactoin Reports at FDA," (1986) Drug. Inf. J., vol. 20, pp. 147-150.
Van Poppel et al., "A One-Year, Multicentre, Randomised Study of Degarelix a Gonadatrophin-Releasing Hormone (GNRH) Receptor Blocker, in Prostate Cancer Patients" Eur Urol Supppl 2005:5(2):251.
Van Poppel, "Evaluation of degarelix in the management of prostate cancer," Cancer Management and Research, vol. 2, pp. 39-52, 2010.
Wilson, et al., "Leuprolide acetate: a drug of diverse clinical applications," Expert Opin. Investig. Drugs, (2007), vol. 16, pp. 1851-1863.
Wilson, et al., "Prediction of Coronary Heart Disease Using Risk Factor Categories," (1998) Circulation, 97:1837-47.
Wolff, et al., "Cumulative analysis from six comparative randomised clinical trials of degarelix versus luteinising hormone-releasing hormone (LHRH) agonists: Better PSA-progressionfree survival confirmed in trials an everyday practice," (2012).
Yannucci, et al., "The Effect of Androgen Deprivation Therapy on Fasting Serum Lipid and Glucose Parameters," (2006) J. Urol., vol. 176, pp. 520-525.
Crawford et al., Degarelix versus LHRH agonist: Differential skeleton and urinary tract outcomes for man analysis of size comparative randomized clinical trials, J. Clin. Oncol 31 (suppl 6; abstr 68) (2013).
Heidenreich et al., "Welche Mechanismen Liegen Der Besseren Kontrolle Des Psa-Progressionsfreien Uberlebens Von Degarelix Im Vergleich Mit Leuprorelin Zugrunde?", RWTH, Aache, Ferring Arzneimittel GmbH, Kiel, 4 pages (2013).
Kongress der Nordrhein-Westfalisch Gesellschaft fur Urologie, p. 33, Heidenreich et al., "Welche Mechanismen Liegen Der Besseren Kontrolle Des Psa-Progressionsfreien Uberlebens Von Degarelix Im Vergleich Mit Leuprorelin Zugrunde?", RWTH, Aache, Ferring Arzneimittel GmbH, Kiel, 4 pages. (2013). (Apr. 13, 2013).
Co-pending U.S. Appl. No. 13/381,762.
Co-pending U.S. Appl. No. 13/458,330.
Co-pending U.S. Appl. No. 13/881,744.
Co-pending U.S. Appl. No. 13/881,751.
fda.gov, Label for Degarelix for injection, Dec. 24, 2008, available at www.accessdata.fda.gov/drugsatfda_docs/label/2008/022201lbl.pdf, last visited Jun. 4, 2013.
International Search Report issued on Apr. 19, 2012, in Application No. PCT/EP2012/050695.
Iversen et al., "Improved outcomes with degarelix monotherapy compared with luteinizing hormone-releasing hormone (LHRH) agonists plus antiandrogen in the treatment of men with advanced prostate cancer" , 29th Congress of the Scandinavian Association of Urologists, 2 pages (May 22, 2013).
Malkin, "Are techniques used for intramuscular injection based on research evidence?" Nursing Times, Dec. 16, 2008, http://www.nursingtimes.net/nursing-practice/clinical-zones/prescribing/are-techniques-used-for-intramuscular-injection-based-on-research-evidence/1952004.article.
Office Action dated Jul. 25, 2013, U.S. Appl. No. 12/829,467.
Office Action dated Jul. 26, 2013, U.S. Appl. No. 12/901,270.
Office Action dated Jun. 11, 2013, U.S. Appl. No. 13/381,762.
Office Action dated Jun. 6, 2013, U.S. Appl. No. 12/774,113.
People's Republic of China First Office Action in corresponding Application No. 201080019696.2, 2 pages (Feb. 25, 2013).
Wiegel et al., "Neoadjuvant Androgen Deprivation Therapy for Prostate Volume Reduction, Lower Urinary Tract Symptom Relief and Quality of Life Improvement in Men with Intermediate- to High-risk Prostate Cancer: A Randomised Non-inferiority Trial of Degarelix versus Goserelin plus Bicalutamide," Clin. Oncol., vol. 25, No. 3, pp. 190-196 (Mar. 2013).
Albertsen, et al. "Cardiovascular Morbidity Associated with Gonadotropin Releasing Hormone Agonist and an Antagonist," European Urology (2013), https://dx.doi.org/10.16/j.eururo.2013.10,032.
Crawford et al., Degarelix Versus LHRH Agonists: Differential Skeletall Morbidity Outcomes from a Pooled Analysis of Six Comparative Randomised Clinical Trials (2012).
Office Action (final) dated Oct. 8, 2013, U.S. Appl. No. 13/381,762.
Office Action dated Sep. 3, 2013, in U.S. Appl. No. 13/458,330.
Office Action mailed Dec. 3, 2013, in copending U.S. Appl. No. 12/368,713.

* cited by examiner

PHARMACEUTICAL COMPOSITIONS AND METHODS FOR THE TREATMENT OF PROSTATE CANCER

This application claims priority to U.S. Provisional Application No. 61/187,819 filed Jun. 17, 2009, and European Patent Application EP09251242.5, filed on May 1, 2009, all of which are incorporated herein by reference in their entireties.

The present disclosure relates to pharmaceutical compositions and methods for the treatment of prostate cancer.

Prostate cancer is a leading cause of mortality and morbidity for men in the industrialized world. The majority of prostate cancers are dependent on testosterone for growth and the current medical approach in the management of advanced prostate cancer involves androgen deprivation. The aim is to reduce serum testosterone (T) to below castrate level (T≤0.5 ng/mL). This may be achieved by, for example, bilateral orchidectomy or by the administration of gonadotrophin releasing hormone (GnRH) receptor agonists.

Gonadotrophin releasing hormone (GnRH) is a natural hormone produced by the hypothalamus that interacts with a receptor in the pituitary to stimulate production of luteinising hormone (LH). To decrease LH production, agonists of the GnRH receptor (GnRH-R), such as leuprolide (Lupron) and goserelin, have been developed. Such GnRH-R agonists initially act to stimulate LH release and only after prolonged treatment act to desensitize GnRH-R such that LH is no longer produced, ultimately causing suppression of testosterone production by the testes. However, the initial stimulation of LH production by the agonist leads to an initial surge in the production of male sex hormones. This phenomenon, known as the "testosterone surge" or "flare reaction," can last for as long as two to four weeks, and may stimulate the prostate cancer; it can lead to a worsening of current symptoms or appearance of new symptoms such as spinal cord compression, bone pain and urethral obstruction. One approach that has been taken to avoid this problem has been to combine administration of a GnRH-R agonist with an antiandrogen, such as flutamide or bicalutamide, known as total androgen ablation therapy (AAT). The use of antiandrogens, however, is associated with serious hepatic and gastrointestinal side effects.

Antagonists of the gonadotrophin releasing hormone receptor (GnRH-R) have been developed to overcome the "testosterone surge" or "flare reaction" associated with GnRH agonists. GnRH antagonists competitively bind to and block the GnRH receptors and cause a rapid decrease of LH and Follicle Stimulating Hormone (FSH) excretion, thereby reducing testosterone production with no initial stimulation/surge. However, GnRH antagonist peptides are frequently associated with the occurrence of histamine-releasing activity.

While the use of both GnRH agonist and antagonists in androgen deprivation therapy to treat prostate cancer has yielded promising results, there are concerns about the relative safety of the available drugs. For example, the GnRH antagonist Abarelix™ was found to carry a risk of serious allergic reactions, including anaphylaxis with hypotension and syncope, and was also found to lose efficacy over the course of treatment in some cases. Indeed, Abarelix™ (Plenaxis™ in the U.S.) was eventually approved, but only for selected patients with advanced prostate cancer, and was eventually withdrawn from the market in 2005 for commercial reasons apparently related to these problems. In particular, it has been suggested that certain androgen deprivation therapies could adversely affect cardiovascular health (see Yannucci et al. (2006) *J. Urology* 176:520-525; and Etzioni et al. (1999) *J. Natl. Canc. Inst.* 91:1033).

Applicants developed a third generation GnRH antagonist, degarelix, for treatment of prostate cancer. Degarelix is a synthetic decapeptide antagonist of GnRH. A long term evaluation in a multicentre randomised study demonstrated that degarelix is effective and well-tolerated without evidence of systemic allergic reactions. Koechling, et al., "Effect of various GnRH antagonists on histamine release from human skin"; Poster, 8$^{th}$ Int. Symp. GnRH Analogues in Cancer & Human Rep.; subm. European J. Pharm., March 2009. An application for marketing authorisation/new drug application for a formulation for monthly administration was submitted to the FDA and EMEA on 27 Feb. 2008. Marketing Authorisation was granted by the FDA on 24 Dec. 2008, and by EMEA on 27 Feb. 2009.

There is, however, a need for a treatment regimen which maintains serum testosterone below 0.5 ng/mL long term (e.g. for periods of 1 year or longer) while minimising the administration requirements (and hence reducing the requirement for e.g. monthly hospital visits for the patient).

Applicants found that to maintain serum testosterone below 0.5 ng/mL (i.e. prevent testosterone breakthrough) over a longer period, degarelix may be administered in such a way that the median plasma trough concentration (of degarelix) is maintained above 9-10 ng/ml, preferably above 11 or 12 or 13 ng/mL (see FIG. 1). Simply increasing the dose, however, is not straightforward because of the risk of side effects and also because the dose size may become unmanageable.

Degarelix is formulated as a powder (of degarelix acetate) which is reconstituted as a solution for subcutaneous injection. It is reconstituted with Water for Injection ("WFI") or, depending on the degarelix dose and concentration, with mannitol solution (e.g. 2.5% or 5%) in order to maintain isotonicity.

In aqueous media, at concentrations of 5 mg/mL or above, degarelix acetate demonstrates nucleation dependent fibrillation, which confers to the substance its ability to form an in vivo gel-like depot at the injection site. Thus, on coming into contact with body tissues such as plasma, degarelix spontaneously forms a gel depot. Degarelix is then released from the depot by diffusion in a sustained manner. Degarelix fibrillation follows a nucleation dependent mechanism, and the properties of the depot are therefore primarily related to the degarelix concentration.

It has been proposed that degarelix is released from the depot in two phases: a fast release immediately after dosing, accounting for high initial plasma concentration levels; and a slow release phase which determines the plasma concentration levels in the maintenance phase. In pharmacokinetic (PK) modeling of degarelix, these two distinct phases have been described as two first-order input phases controlling the release from the depot: a fast input to account for the initial fast release described by the fast absorption half-life and a slow input to account for the prolonged phase observed described by the slow absorption half-life.

Generally, the area under the concentration-time curve (AUC) is related to both dose and concentration of the injection solution. The AUC increases with increasing dose, but if the concentration of the injection solution is increased there is a decrease in the AUC. Thus, with respect to degarelix, the absolute bioavailability has been estimated to be 43.4%, 40.0%, 31.1%, 27.4%, and 21.3% when using a dose concentration of 10, 20, 30, 40, and 60 mg/mL, respectively; increasing the concentration decreases the overall bioavailability.

Applicants unexpectedly found that administration of degarelix at a defined dose and defined concentration, for example, as applied at the maintenance phase, is associated with slower release characteristics of degarelix from the resulting depot (as well as the overall decrease in bioavailability of the degarelix discussed above). This surprising effect means that administration of defined doses of degarelix at the defined concentrations provide a depot which releases sufficient degarelix to achieve the desired therapeutic effect (i.e. the required plasma concentration), but releases in a manner that the plasma concentration is maintained at the therapeutically effective level over a period of time (e.g. three months or above, given sufficient starting dose) without monthly injections. Increasing the concentration of the degarelix means the injection size is manageable even at these higher doses, with the unexpected benefit that the sustained release capabilities are actually increased.

SUMMARY

In accordance with the disclosure, Applicants developed a pharmaceutical composition for administration of degarelix at a defined dose and defined concentration which, when administered according to the disclosure, may provide sustained release of degarelix without the need for monthly injections to achieve a therapeutic plasma concentration.

Thus, according to the present disclosure in one aspect, there is provided a pharmaceutical composition comprising degarelix or a pharmaceutically acceptable salt thereof (e.g. acetate), an excipient (e.g. co-lyophilisate, e.g. sugar, e.g. mannitol), and a solvent (e.g. aqueous solvent, e.g. water), wherein the concentration of degarelix or pharmaceutically acceptable salt thereof ranges from 50 mg to 80 mg of degarelix per mL of solvent.

The degarelix (or pharmaceutically acceptable salt thereof) is for administration as a liquid solution in a solvent, e.g. an aqueous solvent, e.g. water (e.g., WFI), or a solution of water and mannitol etc. The starting and maintenance doses may be for administration by injection. The maintenance dose may be administered as two injections, each containing (substantially) half of the maintenance dose.

The pharmaceutical composition may provide a therapeutically active mean plasma trough concentration of degarelix (a plasma concentration of 9 ng/mL or above, preferably 10 ng/mL or above, e.g. 12 mg/mL or above, as measured by techniques well known in the art), for example from 28 days after the starting dose, and may maintain this therapeutically active concentration for e.g., at least 365 days and/or the duration of the treatment. Herein, the term "duration of the treatment" means for as long as the maintenance doses are administered; thus "maintain this therapeutically active concentration for the duration of the treatment" means that the therapeutically active concentration is maintained at least until the last maintenance dose is administered. The composition may reduce the serum testosterone level of the patient to 0.5 ng/mL or below (i.e., from 0 ng/mL to 0.5 ng/mL), for example from 3 days, for example from 7 days, for example from 14 days, for example from 28 days after the starting dose, and may maintain the serum testosterone level at 0.5 ng/mL or below for e.g. at least 365 days and/or the duration of the treatment with the administration of at least one maintenance dose.

Other studies establish that degarelix or pharmaceutically acceptable salt thereof at a dose of 240 mg (40 mg/mL) is an effective starting dose. In one-month dosing regimen studies, two (monthly) maintenance doses of degarelix or pharmaceutically acceptable salt thereof at 160 mg (40 mg/mL) and 80 mg (20 mg/mL) demonstrated to be effective with testosterone response rates of 100% and 98%, respectively from Day 28 to Day 364 with monthly maintenance doses. However, doses of 240 mg, 160 mg or 80 mg failed to sustain testosterone suppression for 3 months following an injection of the starting dose. Thus, with a starting dose of degarelix or pharmaceutically acceptable salt thereof of 240 mg (with a concentration of 40 mg/mL of solvent), an additional dose would be required before 3 months (e.g., at Day 28). Simulation of a 'true' three-month dosing schedule with 480 mg [i.e. starting dose of 480 mg with further doses at 3, 6, 9 months] suggests that the trough PK level (degarelix concentration) will be around 8 ng/mL, which is insufficient. With dosing at 0 months and an additional dosage at 1 month, it is believed that a steady state level is reached faster and this is (together with formulation, dose and concentration) a factor for consideration to obtain and maintain therapeutic levels in the patient. Use of a higher dose as the starting dose to have a 'true' 3 month depot is not feasible because of the combined requirements of a sufficient starting/loading phase release to allow buildup of degarelix plasma concentration; and at the same time sufficient long term release to achieve sufficiently high steady state concentration for 3 months. Applicants surprisingly found that the defined maintenance compositions may provide a therapeutically active mean plasma concentration of degarelix (a plasma trough concentration of 9 ng/mL or above), for example from 28 days after the starting dose, and may maintain this therapeutically active concentration for e.g. at least 365 days and/or the duration of the treatment with the administration of at least one maintenance dose, without the need for monthly maintenance doses. More surprisingly, Applicants' defined pharmaceutical compositions (when used in this way) and their use in treatment may not be associated with an increase in injection related side effects (compared to administration of a dose of 240 mg degarelix at a concentration of 40 mg/mL with monthly administration). This is surprising given the high doses (and concentrations) of degarelix in the defined maintenance dose(s).

The concentration of the maintenance dose of degarelix or a pharmaceutically acceptable salt thereof may be from 50 to 80 mg per mL of solvent, e.g., 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80 mg/mL or any number between, e.g. 55 to 65 mg of degarelix per mL of solvent. Applicants found that administration of maintenance doses of degarelix or pharmaceutically acceptable salt thereof (e.g. acetate) [formed by dissolution of a lyophilisate comprising degarelix and excipient (e.g. a co-lyophilisate e.g. mannitol) in a solvent e.g. water] of e.g., a dose of degarelix at 360 mg, 480 mg with a concentration from, e.g., 55 to 65 mg degarelix/mL solvent, e.g. 60 mg/mL may be effective. The administration of maintenance doses of degarelix or a pharmaceutically acceptable salt thereof of 480 mg at a concentration of 60 mg degarelix/mL solvent at 84 day (3 monthly) intervals (e.g., commencing with the first maintenance dose 28 days (one month) after the starting dose) may provide effective suppression of testosterone (i.e., reduction of testosterone to below 0.5 ng/mL and maintenance below this level with prevention of testosterone breakthrough) for periods of up to 1 year or longer, without likelihood of adverse effects. The lack of side effects is remarkable given the relatively high doses and two injections; surprisingly, there is no increase in injection related side effects compared with the lower 1 month doses (which are one injection).

According to the present disclosure in a further aspect, there is provided a kit comprising: at least one starting container comprising a lyophilisate of degarelix or a pharmaceutically acceptable salt thereof and an excipient, wherein the lyophilisate of degarelix or pharmaceutically acceptable salt thereof is present in an amount ranging from 200 mg to 300 mg; at least one maintenance container comprising a lyophilisate of degarelix or a pharmaceutically acceptable salt thereof and an excipient, wherein the lyophilisate of degarelix or a pharmaceutically acceptable salt thereof is present in an amount ranging from 320 mg to 550 mg; and at least one container comprising a solvent. In one example, a kit may provide a solution having 480 mg degarelix at a concentration of 60 mg/mL. The kit may comprise, for example, two containers (e.g. vials) of 240 mg degarelix and, for example, a container (vial, prefilled syringe) of liquid (e.g., 6 mL or 10 mL WFI); optionally, the kit may also comprising an administration apparatus (e.g., injection apparatus), for example, syringe and/or safety needle, cannula, etc. The kit may further comprise an transfer apparatus (i.e., for improving transfer) to transfer solvent between the container(s) (e.g., prefilled syringe, vial) of solvent and the container(s) (e.g., vial) of degarelix; the transfer apparatus may be, e.g., an adapter. The kit optionally includes a device for improving or enhancing reconstitution (e.g., a swirling device). In a further example, the kit may comprise two containers (e.g., vials) of 240 mg degarelix (as lyophilisate with excipient) and, for example, two prefilled syringes, each including WFI (4.2 mL). A person of ordinary skill in the art will readily appreciate that mixing each vial of degarelix with e.g. 4.2 mL WFI will provide a 4 mL solution of about 240 mg degarelix at a concentration of 60 mg/mL of solvent, and the two vials will together make up 8 mL of maintenance dose for injection as a single or, more preferably, as two injection(s).

In a further example, the kit according to the present disclosure comprises: at least one first container comprising a lyophilisate of degarelix or a pharmaceutically acceptable salt thereof and an excipient, wherein the lyophilisate of degarelix or a pharmaceutically acceptable salt thereof is present in an amount ranging from 320 mg to 550 mg; and at least one second container comprising a solvent.

According to the present disclosure in a still further aspect, there is provided a method of preparing a starting concentration and a maintenance concentration for treating prostate cancer in a patient in need thereof comprising: combining at least one starting container comprising a lyophilisate of degarelix or a pharmaceutically acceptable salt thereof and an excipient with at least one container comprising a solvent, wherein the lyophilisate of degarelix or the pharmaceutically acceptable salt thereof and the excipient are dissolved in the solvent to achieve a concentration range from 20 mg to 80 mg of degarelix per mL of the solvent to form the starting concentration; combining, after an interval ranging from 14 to 56 days of forming the starting dose, at least one maintenance container comprising a lyophilisate of degarelix or a pharmaceutically acceptable salt thereof and an excipient with at least one second container comprising a solvent, wherein the lyophilisate of degarelix or the pharmaceutically acceptable salt thereof and the excipient are dissolved in the solvent to achieve a concentration range from 50 mg to 80 mg of degarelix per mL of the solvent to form the maintenance concentration; and repeating, at least once, the combination of the at least one maintenance container with the at least one container comprising a solvent to form the maintenance concentration, after an interval ranging from 56 days to 112 days from the combination of the prior maintenance dose.

In yet another example, there is recited a method of preparing a pharmaceutical composition for treating prostate cancer comprising: combining at least one first container comprising a lyophilisate of degarelix or a pharmaceutically acceptable salt thereof and an excipient with at least one second container comprising a solvent, wherein the lyophilisate of degarelix or the pharmaceutically acceptable salt thereof and the excipient are dissolved in the solvent to achieve a concentration range from 40 to 80 mg, such as from 50 mg to 80 mg of degarelix per mL of the solvent to form a maintenance concentration.

Regarding the maintenance concentration, the method of preparation may provide a solution having concentration of degarelix between 50 and 80 mg/mL, e.g. 55 to 65 mg/mL, e.g. 56, 57, 58, 59, 60, 61, 62, 63, or 64 mg of degarelix per mL of solvent, or any number in between. The dose of degarelix may range from 320 mg to 550 mg (e.g. from 350 mg to 520 mg; e.g. from 440 mg to 490 mg). The dose of degarelix may be, for example, 240 mg (starting dose), 360 mg (maintenance dose) or 480 mg (maintenance dose).

According to the present disclosure in yet a further aspect, there is provided a method of treating prostate cancer in a patient in need thereof comprising: administering to the patient a starting dose comprising degarelix or a pharmaceutically acceptable salt thereof, an excipient, and a solvent, wherein the starting dose ranges from 200 mg to 300 mg of degarelix or pharmaceutically acceptable salt thereof at a concentration ranging from 20 mg to 80 mg of degarelix per mL of the solvent; administering to the patient, at an interval ranging from 14 to 56 days after the administration of the starting dose, a maintenance dose comprising degarelix or a pharmaceutically acceptable salt thereof, an excipient, and a solvent, wherein the maintenance dose ranges from 320 mg to 550 mg of degarelix or a pharmaceutically acceptable salt thereof at a concentration ranging from 50 mg to 80 mg of degarelix per mL solvent; and repeating, at least once, the administration of the maintenance dose to the patient, after an interval ranging from 56 days to 112 days from the administration of the prior maintenance dose.

In one example, a method of treating prostate cancer in a patient in need thereof comprising: administering to the patient a starting dose comprising degarelix or pharmaceutically acceptable salt thereof, an excipient, and a solvent, wherein the starting dose is 240 mg of degarelix or a pharmaceutically acceptable salt thereof at a concentration of 40 mg of degarelix per mL of the solvent; administering to the patient, 28 days after the administration of the starting dose, a maintenance dose comprising degarelix or pharmaceutically acceptable salt thereof, an excipient, and a solvent, wherein the maintenance dose is 480 mg of degarelix or a pharmaceutically acceptable salt thereof at a concentration of 60 mg of degarelix per mL solvent; and repeating, at least once, the administration of the maintenance dose to the patient 84 days after the administration of the prior maintenance dose.

In yet a further example, a method of treating prostate cancer in a patient in need thereof comprising: administering to the patient a starting dose comprising degarelix or a pharmaceutically acceptable salt thereof, an excipient, and a solvent, wherein the starting dose is 240 mg of degarelix or pharmaceutically acceptable salt thereof at a concentration of 40 mg of degarelix per mL of the solvent; administering to the patient, 28 days after the administration of the starting dose, a maintenance dose comprising degarelix or pharmaceutically acceptable salt thereof, an excipient, and a solvent, wherein the maintenance dose is 360 mg of degarelix or a pharmaceutically acceptable salt thereof at a concentration of 60 mg of degarelix per mL solvent; and repeating, at least once, the administration of the maintenance dose to the patient 84 days after the administration of the prior maintenance dose.

The degarelix or the pharmaceutically acceptable salt thereof may be administered at a starting dose ranging from 200 mg and 300 mg; followed by a maintenance dose ranging from 320 mg to 550 mg administered 28 days (i.e., one month) after the administration of the starting dose; followed by one or more (i.e., at least one) further maintenance dose(s) ranging from 320 mg to 550 mg of degarelix or pharmaceutically acceptable salt thereof at a time interval of 84 days (i.e., three months) between maintenance dose(s).

The concentration of the maintenance dose(s) of degarelix or a pharmaceutically acceptable salt thereof ranges from 50 mg/mL to 80 mg/mL, for example, from 55 mg/mL to 65 mg/mL of solvent.

It is to be understood that both the foregoing general description and the following detailed description are exemplary and explanatory only and are not restrictive of the disclosure, as claimed.

DESCRIPTION

Terms and Definitions

Particular aspects of the disclosure are described in greater detail below. The terminologies and definitions as used in the present application as clarified herein are intended to represent the meaning of the Applicants in their disclosure of the disclosure. The patent and scientific literature referred to herein are hereby incorporated by reference in their entireties. The terms and definitions provided herein control, if in conflict with terms and/or definitions incorporated by reference.

The singular forms "a," "an," and "the" include plural reference unless the context indicates otherwise.

The terms "approximately" and "about" mean to be nearly the same as a referenced number or value. As used herein, the terms "approximately" and "about" should be generally understood to encompass ±10% of a specified amount, frequency or value. With regard to the trough plasma level, it should be understood that specific values described herein for subject populations represent a median or mean value, unless otherwise noted. Accordingly, aspects of the disclosure requiring a particular value level in a subject are substantially supported herein by population data in which the value is assessed to be a meaningful delimitation of the subject population.

Herein, the terms "initial dose", "starting dose" and "loading dose" are used interchangeably. The term "plasma concentration" means "plasma trough concentration."

One treatment month is generally regarded as, and used in the presently described clinical trial results, meaning 28 days. As such, two months refer to 56 days, three months refer to 84 days, four months refer to 112 days, and so on.

The term "prostate cancer" refers to any cancer of the prostate gland in which cells of the prostate mutate and begin to multiply out of control. The term "prostate cancer" includes early stage, localized, cancer of the prostate gland; later stage, locally advanced cancer of the prostate gland (in which the cancer cells spread (metastasize) from the prostate to other parts of the body, especially the bones and lymph nodes).

The term "prostate-specific antigen" or "PSA" refers to a protein produced by the cells of the prostate gland that is present in small quantities in the serum of normal men, but is often elevated in the presence of prostate cancer and in other prostate disorders. A blood test to measure PSA is the most effective test currently available for the early detection of prostate cancer. Higher than normal levels of PSA are associated with both localized and metastatic prostate cancer.

The term "administer," "administration," or "administering" as used herein refer to (1) providing, giving, dosing and/or prescribing by either a healthcare practitioner or his or her authorized agent or under his or her direction degarelix, and (2) putting into, taking, or injecting by the patient or person himself or herself, degarelix.

Degarelix and Related Pharmaceutical Formulations

Degarelix is a potent GnRH antagonist that is an analog of the GnRH decapeptide (pGlu-His-Trp-Ser-Tyr-Gly-Leu-Arg-Pro-Gly-NH$_2$) incorporating p-ureido-phenylalanines at positions 5 and 6 (Jiang et al. (2001) *J. Med. Chem.* 44:453-67). It is indicated for treatment of patients with prostate cancer in whom androgen deprivation is warranted (including patients with rising prostate specific antigen (PSA) levels after having already undergone prostatectomy or radiotherapy).

Degarelix is a selective GnRH receptor antagonist (blocker) that competitively and reversibly binds to the pituitary GnRH receptors, thereby rapidly reducing the release of gonadotrophins and consequently testosterone (T). Prostate cancer is sensitive to testosterone deprivation, a mainstay principle in the treatment of hormone-sensitive prostate cancer. Unlike GnRH agonists, GnRH receptor blockers do not induce a luteinizing hormone (LH) surge with subsequent testosterone surge/tumor stimulation and potential symptomatic flare after the initiation of treatment.

The active ingredient degarelix is a synthetic linear decapeptide amide containing seven unnatural amino acids, five of which are D-amino acids. The drug substance is an acetate salt, but the active moiety of the substance is degarelix as the free base. The acetate salt of degarelix is a white to off-white amorphous powder (of low density as obtained after lyophilisation). The chemical name is D-Alaninamide, N-acetyl-3-(2-naphthalenyl)-D-alanyl-4-chloro-D-phenylalanyl-3-(3-pyridinyl)-D-alanyl-L-seryl-4-[[[(4S)-hexahydro-2,6-dioxo-4-pyrimidinyl]carbonyl]amino]-L-phenylalanyl-4-[(aminocarbonyl)amino]-D-phenylalanyl-L leucyl-N6-(1-methylethyl)-L-lysyl-L-prolyl. It has an empirical formula of $C_{82}H_{103}N_{18}O_{16}Cl$ and a molecular weight of 1,632.3 Da. The chemical structure of degarelix has been previously shown (e.g., EP 1003774, U.S. Pat. No. 5,925,730, U.S. Pat. No. 6,214,798) and may be represented by the formula:

Ac-D-2NaI-D-4Cpa-D-3Pal-Ser-4Aph(Hor)-D-4Aph(Cbm)-Leu-Lys(iPr)-Pro-D-Ala-NH$_2$.

Degarelix may be formulated for administration subcutaneously (as opposed to intravenously) or intramuscularly, generally in the abdominal region. As with other drugs administered by subcutaneous injection, the injection site may vary periodically to minimize, among other things, injection site discomfort. In general, injections should be given in areas where the patient will not be exposed to pressure, e.g., not close to waistband or belt and not close to the ribs.

Administration of degarelix by subcutaneous or intramuscular injection works well, but daily injections are generally not preferred by the patient and so a depot formulation of degarelix may be utilized as described in International Publication No. WO 03/006049 and U.S. Pub. Nos. 2005/0245455 and 2004/0038903. Briefly, subcutaneous administration of degarelix may be conducted using a depot technology in which the peptide is released from a biodegradable polymer matrix over a period of time (typically) ranging one month from three months. Degarelix (and related GnRH antagonist peptides) have a high affinity for the GnRH receptor and are much more soluble in water than other GnRH analogues. Degarelix and these related GnRH antagonists are capable of forming a gel after subcutaneous injection, and this gel can act as a depot from which the peptide is released over a period of weeks or even months.

Degarelix may be provided as a powder for reconstitution (with an excipient) by a solution for injection. The dissolved solution with degarelix and the excipient is used for subcutaneous or intramuscular injection, e.g., to form a depot when injected into the patient for treatment as described above. The powder form of degarelix or pharmaceutically acceptable salt thereof may be provided as a lyophilisate containing degarelix (e.g. as acetate) and mannitol as the excipient. An example of a suitable solvent is water (e.g., water for injection (WFI)). The lyophilisate of degarelix may be provided in a kit comprising at least one starting container, at least one maintenance container, and at least one container comprising a solvent.

The solvent may be provided in a container(s) or vessel(s) (e.g., vials), that may include various amounts of solvent, e.g. containing 6 mL water. For example, degarelix in the lyophilisate form may be provided in a vial containing 120 mg degarelix (acetate) for reconstitution with 3 mL WFI such that each mL of solution contains about 40 mg degarelix; reconstituting gives a 3 mL solution for injection containing about 120 mg degarelix. Injection of two such solutions provides a starting dose of about 240 mg degarelix at a concentration of 40 mg/mL of solvent.

In another example, degarelix in the lyophilisate form may be provided in a vial containing 240 mg degarelix (acetate). After reconstitution with about 4 mL WFI, each mL solution contains about 60 mg degarelix. Injection of two such solutions provides a maintenance dose of about 480 mg degarelix of concentration 60 mg/mL.

In another example, degarelix in the lyophilisate form may be provided in a vial containing 180 mg degarelix (acetate). After reconstitution with about 3 mL WFI, each mL of solution contains about 60 mg degarelix. Injection of two such solutions provides a maintenance dose of about 360 mg degarelix of concentration 60 mg/mL. The reconstituted solution ready for injection should be perceived as a visually clear liquid.

The dosing regimen for degarelix (i.e., the method of treating prostate cancer in a patient in need thereof) may be administered as a starting dose comprising degarelix or pharmaceutically acceptable salt thereof, an excipient, and a solvent. The starting dose ranges from 200 mg to 300 mg of degarelix or pharmaceutically acceptable salt thereof, such as 200 mg, 220 mg, 240 mg, 260 mg, 280 mg, 300 mg, or any number in between and further for example, the starting dose may be 240 mg of degarelix or pharmaceutically acceptable salt thereof. The starting concentration of degarelix or pharmaceutically acceptable salt thereof ranges from 20 mg/mL to 80 mg/mL of solvent, for example, 20 mg/mL, 30 mg/mL, 40 mg/mL, 50 mg/mL, 60 mg/mL, 70 mg/mL, 80 mg/mL, or any number in between and further for example, the starting concentration may be 40 mg/mL of solvent. In an example, the dosing regimen for degarelix may be administered as a starting dose of 240 mg as two injections of 3 mL of about 40 mg/mL of solvent.

After administration of the starting dose, a maintenance dose follows at an interval ranging from 14 to 56 days, such as 14 days, 28 days, 56 days, or any interval in between and further for example, at an interval of 28 days. The maintenance dose comprises degarelix or pharmaceutically acceptable salt thereof, an excipient, and a solvent. The maintenance dose ranges from 320 mg to 550 mg of degarelix or pharmaceutically acceptable salt thereof, for example, from 320 mg, 340 mg, 360 mg, 380 mg, 400 mg, 420 mg, 440 mg, 460 mg, 480 mg, 500 mg, 520 mg, 540 mg, 550 mg, or any number in between, and further for example, 360 mg or 480 mg of degarelix or pharmaceutically acceptable salt thereof. The maintenance concentration of degarelix or pharmaceutically acceptable salt thereof ranges from 50 mg/mL to 80 mg/mL, such as from 50 mg/mL, 55 mg/mL, 60 mg/mL, 65 mg/mL, 70 mg/mL, 75 mg/mL, 80 mg/mL, or any number in between and further for example, 60 mg/mL of degarelix or pharmaceutically acceptable salt thereof. In an example, the dosing regimen for degarelix may be administered as a maintenance dose, after the administration of the starting dose, of 360 mg or 480 mg of degarelix or pharmaceutically acceptable salt thereof as two injections of 4 mL of about 60 mg/mL of solvent.

The at least one additional maintenance dose may be administered after the administration of the maintenance dose at an interval ranging from 56 days to 112 days, such as 56 days, 84 days, 112 days, or any interval in between and further for example, 84 days. The administration of the at least one maintenance dose may continue as needed (e.g., maintenance doses may be administered from 56-112 days after the previous maintenance dose). The additional maintenance dose comprises degarelix or pharmaceutically acceptable salt thereof, an excipient, and a solvent. The additional maintenance dose ranges from 320 mg to 550 mg of degarelix or pharmaceutically acceptable salt thereof, for example, from 320 mg, 340 mg, 360 mg, 380 mg, 400 mg, 420 mg, 440 mg, 460 mg, 480 mg, 500 mg, 520 mg, 540 mg, 550 mg, or any number in between, and further for example, 360 mg or 480 mg of degarelix or pharmaceutically acceptable salt thereof. The additional maintenance concentration of degarelix or pharmaceutically acceptable salt thereof ranges from 50 mg/mL to 80 mg/mL, such as from 50 mg/mL, 55 mg/mL, 60 mg/mL, 65 mg/mL, 70 mg/mL, 75 mg/mL, 80 mg/mL, or any number in between and further for example, 60 mg/mL of degarelix or pharmaceutically acceptable salt thereof.

Administration and Dosage

Throughout the ongoing degarelix development program, population pharmacokinetic/pharmacodynamic (PK/PD) modeling and simulations have been employed to get a better understanding of the PK and PD data, and the relationship between these and other parameters. Results obtained from previous studies demonstrate that a median trough plasma degarelix concentration of 7.34 ng/mL results in 96% of patients achieving serum testosterone (T)≤0.5 ng/mL at Day 28, and that a median plasma concentration of 4.54 ng/mL results in 83% of this same group of patients having T≤0.5 ng/mL at Day 84. Because of the variability in the population, it was considered that this median plasma concentration might not be sufficient to maintain long-term testosterone suppression in approximately 95% of the patients. It was therefore proposed that the dose administered should produce mean serum trough degarelix levels of >9 ng/ml or higher in the Phase 3 studies for the one-month dosing regimen program.

Figure 1:
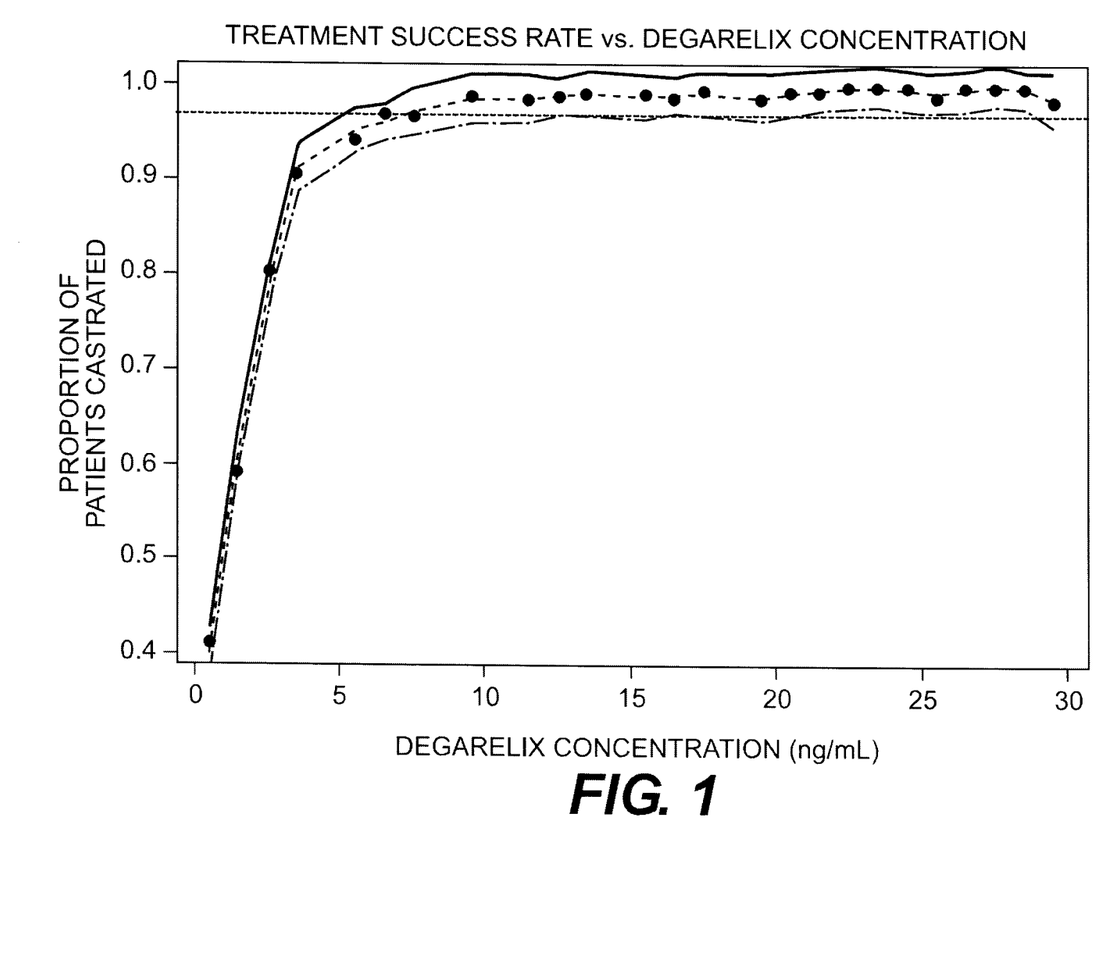
FIG. 1 is a graphical representation of treatment success rate (proportion of patients with testosterone≤0.5 ng/mL) versus plasma degarelix concentration.

The relationship between proportion of patients castrated [(T)≤0.5 ng/mL] and degarelix concentration after day 28 is illustrated in FIG. 1. FIG. 1 is based on data from 1473 prostate cancer patients in clinical studies by dividing PK levels into intervals 0-1, 1-2, 2-3 ng/mL and so forth and plotting observed proportions against PK interval midpoints together with a smoothing line with 95% confidence interval (CI). Based on this information, approximately 97% of the patients are castrated provided that degarelix concentrations stay above a threshold value of 9-10 ng/mL.

In a one-month dosing regimen clinical program, a starting dose of degarelix or pharmaceutically acceptable salt thereof of 240 mg (with a concentration of 40 mg/mL of solvent) exhibited a suppression of testosterone to castrate level (T≤0.5 ng/mL) in 95% of the patients for the first 28 days. A maintenance dose of 80 mg (with a concentration of 20 mg/mL of solvent) degarelix was sufficient for the one-month program. The mean trough levels of patients for the 80 mg (with a concentration of 20 mg/mL of solvent) degarelix maintenance dose were approximately 12 ng/mL. The one-month degarelix dosing program established the dose of 240 mg (with a concentration of 40 mg/mL of solvent) of degarelix or pharmaceutically acceptable salt thereof. Consequently, a starting dose of 240 mg (with a concentration of 40 mg/mL of solvent) was also used later for the three-month dosing regimen studies.

In the one-month dosing regimen studies, two maintenance doses, 160 mg (with a concentration of 40 mg/mL of solvent) and 80 mg (with a concentration of 20 mg/mL of solvent) of degarelix or pharmaceutically acceptable salt thereof, demonstrated effectiveness with testosterone response rates of 100% and 98%, respectively from Day 28 to Day 364. However, none of the doses tested in the one-month dosing regimen program could sustain testosterone suppression for 3 months following an injection. Applicants found that with a starting dose of 240 mg (with a concentration of 40 mg/mL of solvent) of degarelix or pharmaceutically acceptable salt thereof, an additional dose would be required at around day 28.

A three-month dosing regimen Phase 2 study investigated three different dosing regimens. After a starting dose of 240 mg/mL (with a concentration of 40 mg/mL of solvent), a further dose (i.e., maintenance dose) of 240 mg was given on Day 28, and then at Months 3, 6, and 9 or at Months 4, 7, and 10. Maintenance doses of 240 mg were evaluated initially at concentrations of 40 mg/mL and 60 mg/mL in this study, based on the observed results by different PK profiles of different concentrations. The patients were randomized in parallel to one of three different three-month maintenance dosing regimens of degarelix:

240 mg (40 mg/mL) at Months 1, 3, 6, 9;
240 mg (60 mg/mL) at Months 1, 3, 6, 9; or
240 mg (60 mg/mL) at Months 1, 4, 7, 10.

None of the three treatment regimens exhibited a lower limit confidence interval that surpassed the 80% mark; therefore, the primary objective of demonstrating efficacy in achieving and maintaining testosterone at castrate level for one year in at least 80% of patients was not met. Applicants found that a predictor of the time to testosterone>0.5 ng/mL was the degarelix plasma levels during the course of the treatment period. Thus, patients with lower degarelix plasma levels were more likely to have a testosterone level>0.5 ng/mL during the one year treatment period. Analysis of monthly testosterone data indicated that patients remain suppressed at the two visits after dosing, but there is a tendency for testosterone escape (i.e., an increase in testosterone above the 0.5 ng/ml) just before the next dosing at 3 months. Individual patient data showed that most patients who have testosterone breakthrough are suppressed again after re-dosing; this applied to all three treatment groups. This is consistent with the observation that for most patients, the time of first occurrence of a testosterone level>0.5 ng/mL was three months after a previous dose, at the time of trough degarelix plasma levels. The median trough degarelix plasma levels in the study ranged from about 6.5-7.5 ng/mL. This was well below the degarelix level of 9-10 ng/mL considered to be required to maintain testosterone levels at ≤0.5 ng/mL in approximately 95% of patients and indicated that higher maintenance doses of degarelix were needed.

Example

Clinical Trial

The present study included a starting degarelix dose of 240 mg (with a concentration of 40 mg/mL of solvent), followed by maintenance doses of degarelix: i.e., 360 mg (with a concentration of 60 mg/mL of solvent) or 480 mg (with a concentration of 60 mg/mL of solvent), the latter administered at Months 1, 4, 7, and 10. These maintenance doses were relatively higher as compared to the maintenance doses examined in the one-month dosing clinical trial (i.e., 240 mg of degarelix or pharmaceutically acceptable salt thereof).

Prostate Cancer Stage and Duration at Entry

This study completed with 133 patients enrolled (planned enrollment 120). The variables for baseline disease characteristics are summarized for the Phase 2 studies for the three-month dosing regimen in Table 1. There were about 10% of patients who had localized cancer where the treatment was of a curative intent. Most patients had a Gleason score of 7-10, and most patients were normally active as rated on the ECOG performance scale. The mean duration of prostate cancer (PCA) from diagnosis is also shown.

TABLE 1

Stage and Duration of Prostate Cancer at Baseline
(Phase 2, Three-Month Dosing Regimen).

| | Late dose finding (CS18) | |
|---|---|---|
| | 480 mg (N = 66) | 360 mg (N = 67) |
| Stage of PCa at enrolment | N = 66 | N = 67 |
| Localized | 19 (29%) | 26 (39%) |
| Locally advanced | 22 (33%) | 17 (25%) |
| Metastatic | 16 (24%) | 14 (21%) |
| Not complete classification | 9 (14%) | 10 (15%) |
| Curative Intent | N = 66 | N = 67 |
| Yes | 6 (9%) | 7 (10%) |
| No | 60 (91%) | 60 (90%) |
| PCa Stage not complete | N = 9 | N = 10 |
| Curative Intent | 4 (44%) | 3 (30%) |
| Gleason Score | N = 66 | N = 66 |
| 2-4 | 3 (5%) | 8 (12%) |
| 5-6 | 24 (36%) | 19 (29%) |
| 7-10 | 39 (59%) | 39 (59%) |
| PCa Duration | N = 64 | N = 67 |
| Mean (SD) years | 0.725 (1.37) | 1.01 (2.77) |
| Range | (0.057-6.03) | 0.063-20.3) |
| ECOG Performance Score | N = 66 | N = 67 |
| Normal activity | 51 (77%) | 49 (73%) |
| Symptoms, ambulatory | 14 (21%) | 15 (22%) |
| Bedridden <50% | 1 (2%) | 3 (4%) |
| Bedridden >50% | 0 | 0 |
| Bedridden 100% | 0 | 0 |

PCa = prostate cancer

The study was open labeled and patients received a starting dose of 240 mg (with a concentration of 40 mg/mL of solvent) at Month 0 followed by one of two degarelix maintenance dose treatment regimens: 360 mg (with a concentration of 60 mg/mL of solvent) at Months 1, 4, 7, and 10; or 480 mg (with a concentration of 60 mg/mL of solvent) at Months 1, 4, 7, and 10.

The starting dose was administered subcutaneously as two injections of 120 mg (with a concentration of 40 mg/ml of solvent, given as 2×3 mL injections). After 28 days a maintenance dose of 360 mg (with a concentration of 60 mg/mL, given as 2×3 mL injections) or 480 mg (with a concentration of 60 mg/mL, given as 2×4 mL injections) was administered, also in two injections (each of 240 mg). Thereafter, with three monthly intervals, maintenance doses were given, again in the form of two injections. The techniques for reconstitution and subsequent subcutaneous injection of degarelix to form a depot are well known to the skilled man. At each visit, serum testosterone, prostate specific androgen (PSA), and plasma concentration of degarelix were measured by techniques well known in the art.

Table 2 illustrates the cumulative probability of maintaining a testosterone response (T≤0.5 ng/mL) from Day 28 to Day 364 by treatment dose. The higher dose of 480 mg (with a concentration of 60 mg/mL of solvent) showed a numerically greater treatment response (93.3% of patients maintained castrate levels of testosterone) compared to the 360 mg (with a concentration of 60 mg/mL of solvent) dose regimen (89.0%). Although not statistically significantly different, the differences between the two treatment arms in confidence coverage probability of having a true suppression rate greater than the regulatory threshold of 90% is pronounced: the 480 mg treatment arm yields a 79.9% confidence of the true suppression rate being greater than 90%, whereas for the 360 mg treatment arm it is only 39.7%.

TABLE 3

Proportion of Patients with Testosterone ≤ 0.5 ng/mL by Visit - ITT Analysis Set (CS18).

| | Degarelix 480/60 mg | | | Degarelix 360/60 mg | | | Total | | |
|---|---|---|---|---|---|---|---|---|---|
| | N | n | % | N | n | % | N | N | % |
| ITT Analysis Set Day | 66 | | | 67 | | | 133 | | |
| 28 | 62 | 61 | 98.4% | 65 | 64 | 98.5% | 127 | 125 | 98.4% |
| 56 | 61 | 60 | 98.4% | 64 | 64 | 100% | | | |
| 84 | 61 | 60 | 98.4% | 64 | 64 | 100% | | | |
| 112 | 60 | 58 | 96.7% | 63 | 61 | 96.8% | | | |
| 140 | 60 | 59 | 98.3% | 64 | 64 | 100% | | | |
| 168 | 58 | 57 | 98.3% | 63 | 62 | 98.4% | | | |
| 196 | 59 | 58 | 98.3% | 64 | 58 | 90.6% | | | |
| 224 | 58 | 57 | 98.3% | 63 | 62 | 98.4% | | | |
| 252 | 57 | 57 | 100% | 62 | 61 | 98.4% | | | |
| 280 | 55 | 54 | 98.2% | 60 | 56 | 93.3% | | | |
| 308 | 54 | 54 | 100% | 61 | 61 | 100% | | | |
| 336 | 55 | 55 | 100% | 60 | 58 | 96.7% | | | |
| 364 | 54 | 52 | 96.3% | 60 | 57 | 95.0% | | | |

N = Number of patients
n = Number of patients with testosterone ÿ 0.5 ng/mL
% = n/N × 100

Figure 2:
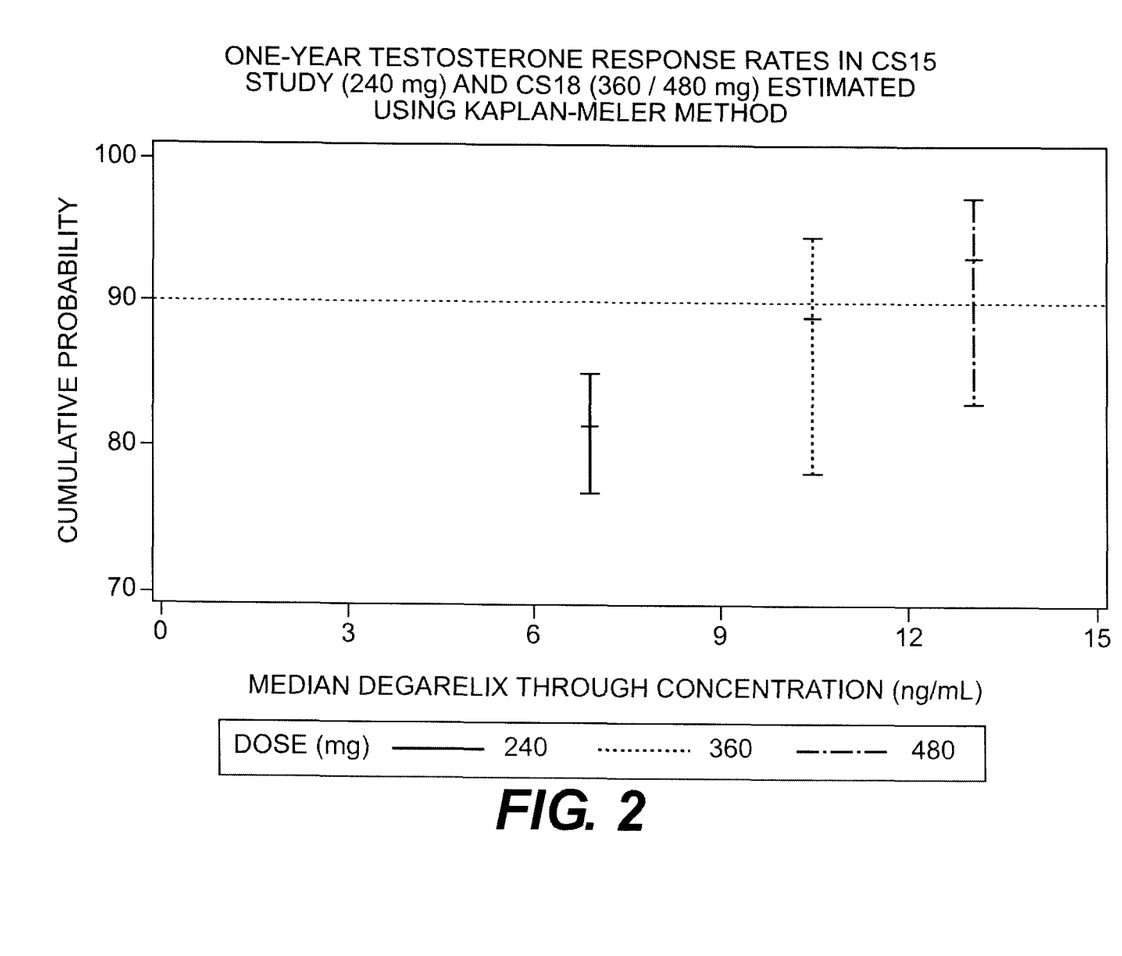
FIG. 2 is a graphical representation of median degarelix trough plasma concentration levels and testosterone responses after various three-month dosing regimens.

FIG. 2 is a graphical representation of median degarelix trough plasma concentration levels and testosterone responses after various three-month dosing regimens. Both doses at 360 mg and 480 mg of degarelix or pharmaceutically acceptable salt thereof exhibited a higher, estimated median degarelix trough concentration above 9 ng/mL compared to the 240 mg dose that is estimated not to rise to the level of 9 ng/mL.

TABLE 2

Cumulative Probability of Testosterone ≤ 0.5 ng/mL from Day 28 to Day 364 - Kaplan-Meier Estimates of Response Rates - ITT Analysis Set (CS18).

| | Degarelix 480/60 mg | | | Degarelix 360/60 mg | | | Total | | |
|---|---|---|---|---|---|---|---|---|---|
| | T > 0.5 ng/mL | Cens | % | T > 0.5 ng/mL | Cens | % | T > 0.5 ng/mL | Cens | % |
| N | 66 | | | 67 | | | 133 | | |
| Day 28 to >364 | 4 | 62 | 93.3% | 7 | 60 | 89.0% | 11 | 122 | 92.8% |
| 95% CI | | | 83.1; 97.4% | | | 78.3; 94.6% | | | 84.5; 95.0% |
| Coverage Probability % | | | 79.9% | | | 39.7% | | | |

T > 0.5 ng/mL = Number of patients with testosterone > 0.5 ng/mL
Cens = Number of censored observations before or at Day 364
(%) = Estimated probability of all testosterone values <= 0.5 ng/mL
Within-treatment group 95% Confidence Interval (CI) calculated by log-log transformation of survivor function Table 3 displays the proportion of patients with a testosterone suppression (T≤0.5 ng/mL) by study visit. The degarelix maintenance dose of 480 mg (with a concentration of 60 mg/mL of solvent) showed sustained testosterone suppression in >95% of patients over the course of the observed time period. The maintenance dose of 360 mg (60 mg/mL) sustained testosterone suppression in at least 90% of patients over the course of the observed time period. The lower values occur just before re-dosing at Month 7 (Day 196, 90.6%) and Month 10 (Day 280, 93.3%). In total, 125 out of 127 patients (98%) showed suppressed testosterone levels below castrate levels at Day 28.

Table 4 displays the median percentage change in PSA by study visit. PSA is a commonly used marker in the diagnosis of prostate cancer and has more recently also been used to monitor response to treatment as well as disease recurrence and progression (Fleming et al. (2006) Nat. Clin. Pract. Oncol. 3: 658-68; Lilja, et al. (2008) Nat. Rev. Cancer 8: 268-78). In general, higher levels of PSA are associated with more severe forms of prostate cancer, with metastatic stage prostate cancer being associated with the highest level of PSA (e.g., >50 ng/mL). Accordingly, rising PSA levels in patients undergoing prostate cancer treatment are associated with incomplete or failed efficacy of the treatment. Here, there were further reductions in PSA after Month 1 and the median reductions were sustained throughout the study period (median reductions of 96-97%).

TABLE 4

Median percentage changes of PSA by monthly visits (CS18).

| | Degarelix 480/60 mg | | Degarelix 360/60 mg | | Total | |
|---|---|---|---|---|---|---|
| | N | Median % Change from Baseline | N | Median % Change from Baseline | N | Median % Change from Baseline |
| ITT Analysis Set Day | 66 | | 67 | | 133 | |
| 28 | 63 | −78.9% | 65 | −83.8% | 128 | −81.2% |
| 56 | 61 | −90.9% | 66 | −93.8% | 127 | −92.9% |
| 84 | 61 | −93.4% | 63 | −95.0% | 124 | −94.5% |
| 112 | 60 | −95.3% | 64 | −95.5% | 124 | −95.4% |
| 140 | 60 | −95.5% | 64 | −96.2% | 124 | −95.9% |
| 168 | 58 | −96.5% | 63 | −96.8% | 121 | −96.6% |
| 196 | 59 | −96.2% | 63 | −95.9% | 122 | −96.2% |
| 224 | 58 | −96.6% | 62 | −96.4% | 120 | −96.5% |
| 252 | 57 | −96.9% | 60 | −97.0% | 117 | −96.9% |
| 280 | 55 | −96.5% | 60 | −97.0% | 115 | −97.0% |
| 308 | 54 | −97.0% | 60 | −97.3% | 114 | −97.2% |
| 336 | 55 | −97.4% | 61 | −97.5% | 116 | −97.4% |
| 364 | 54 | −97.1% | 60 | −96.9 | 114 | −96.9% |
| Last visit | 65 | −96.5% | 66 | −96.9% | 131 | −96.8% |

N = Number of patients

Adverse Events

At the data cut-off date (i.e., seven months after commence of the clinical trial), 133 patients with prostate cancer were exposed to degarelix in the Phase 2, three-month dosing regimen clinical program (CS18).

The common treatment-emergent adverse events reported in >5% of patients in any treatment group in CS18 are summarized as follows (% value being the total of both 480 mg and 360 mg dosage arms):
hot flash (34%),
injection site pain (17%),
weight increase (11%),
hypertension (8%),
injection site erythema (7%),
testicular atrophy (6%),
asthenia (5%),
arthralgia (5%),
fatigue (5%),
gynaecomastia (5%),
pyrexia (4%), and
weight decrease (5%).

Immediate generalized hypersensitivity reactions were reported with earlier GnRH antagonists. There were no immediate anaphylactic reactions reported in this particular degarelix clinical program.

The potential for hepatotoxicity has been extensively evaluated in the clinical program, and as of the data cut-off date, the data do not show any clinically significant impairment of liver function after degarelix treatment.

The incidence of any injection site reaction was 26% in this clinical trial, and the incidence of any injection site reaction was comparable between the two doses. The most frequently reported injection site reaction was injection site pain (17%). Surprisingly, these data are comparable to the results from the one-month dosing regimen clinical program using much lower doses (e.g., 240 mg) of degarelix. Most of the injection site reactions were mild to moderate in intensity (11% each) with 5% of the patients reporting severe injection site reactions. For example, six patients reported severe injection site reactions that identified injection site pain as the severe event.

CONCLUSION

Thus, the data demonstrates the relationship between the pharmacodynamic (PD) dose-response and the pharmacokinetic(PK)/pharmacodynamic association. Higher the median degarelix trough levels (at the end of the one-year treatment or last available measurement) correspond with increased degarelix doses, as compared to the data of the one-month dosing clinical regimen. Median degarelix trough plasma levels of approximately 7 ng/mL, 10 ng/mL, and 13 ng/mL are found with 240 mg (starting dose), 360 mg (maintenance dose), and 480 mg (maintenance dose), respectively. In addition, there were no major differences in the incidence and pattern of adverse events in patients treated with the 360 mg and 480 mg degarelix maintenance doses. On the basis of the testosterone suppression and PK results, the starting and maintenance doses claimed herein and defined represent an effective three-month dosing regimen.

Other embodiments of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. A composition comprising degarelix or pharmaceutically acceptable salt thereof, an excipient, and a solvent, wherein the composition is a dose and the dose of degarelix or pharmaceutically acceptable salt thereof ranges from 320 mg to 550 mg and the concentration of degarelix or pharmaceutically acceptable salt thereof ranges from 60 g to 80 mg of degarelix per mL of the solvent.

2. The composition according to claim 1, wherein the solvent is water.

3. The composition according to claim 1, wherein the excipient is mannitol.

4. The composition according to claim 1, wherein the concentration is 60 mg of degarelix per mL of the solvent.

5. The composition according to claim 1, wherein the dose of degarelix or pharmaceutically acceptable salt thereof ranges from 360 mg to 480 mg.

6. A kit comprising:
at least one starting container comprising a lyophilisate of degarelix or pharmaceutically acceptable salt thereof and an excipient, wherein the lyophilisate of degarelix or pharmaceutically acceptable salt thereof is present in an amount ranging from 200 mg to 300 mg;
at least one maintenance container comprising a lyophilisate of degarelix or pharmaceutically acceptable salt thereof and an excipient, wherein the lyophilisate of degarelix or pharmaceutically acceptable salt thereof is present in an amount ranging from 320 mg to 550 mg; and
at least one container comprising a solvent.

7. The kit according to claim 6, further comprising an administration apparatus.

8. A kit comprising:
at least one first container comprising a lyophilisate of degarelix or pharmaceutically acceptable salt thereof and an excipient, wherein the lyophilisate of degarelix or pharmaceutically acceptable salt thereof is present in an amount ranging from 320 mg to 550 mg; and
at least one second container comprising a solvent.

9. The kit according to claim 8, further comprising an administration apparatus.

10. A method of preparing a starting concentration and a maintenance concentration for treating prostate cancer in a patient in need thereof comprising:
combining at least one starting container comprising a lyophilisate of degarelix or pharmaceutically acceptable salt thereof with a dosage ranging from 200 mg to 300 mg of degarelix and an excipient with at least one container comprising a solvent, wherein the lyophilisate of degarelix or the pharmaceutically acceptable salt thereof and the excipient are dissolved in the solvent to achieve a concentration range from 20 mg to 80 mg of degarelix per mL of the solvent to form the starting concentration;
combining, after an interval ranging from 14 to 56 days from the combination of the starting concentration, at least one maintenance container comprising a lyophilisate of degarelix or pharmaceutically acceptable salt thereof with a dosage ranging from 320 mg to 550 mg of degarelix and an excipient with at least one container comprising a solvent, wherein the lyophilisate of degarelix or the pharmaceutically acceptable salt thereof and the excipient are dissolved in the solvent to achieve a concentration range from 50 mg to 80 mg of degarelix per mL of the solvent to form the maintenance concentration; and
repeating, at least once, the combination of the at least one maintenance container with the at least one container comprising a solvent to form the maintenance concentration, after an interval ranging from 56 days to 112 days from the combination of the prior maintenance concentration.

11. A method of preparing a composition for treating prostate cancer comprising:
combining at least one first container comprising a lyophilisate of degarelix or pharmaceutically acceptable salt thereof and an excipient with at least one second container comprising a solvent, wherein the lyophilisate of degarelix or the pharmaceutically acceptable salt thereof and the excipient are dissolved in the solvent to achieve a concentration range from 50 mg to 80 mg of degarelix per mL of the solvent.

12. A method of treating prostate cancer in a patient in need thereof comprising:
administering to the patient a starting dose comprising degarelix or pharmaceutically acceptable salt thereof, an excipient, and a solvent, wherein the starting dose ranges from 200 mg to 300 mg of degarelix or pharmaceutically acceptable salt thereof at a concentration ranging from 20 mg to 80 mg of degarelix per mL of the solvent;
administering to the patient, at an interval ranging from 14 to 56 days after the administration of the starting dose, a first maintenance dose comprising degarelix or pharmaceutically acceptable salt thereof, an excipient, and a solvent, wherein the maintenance dose ranges from 320 mg to 550 mg of degarelix or pharmaceutically acceptable salt thereof at a concentration ranging from 50 mg to 80 mg of degarelix per mL solvent; and
repeating, at least once, the administration of an additional maintenance dose to the patient, after an interval ranging from 56 days to 112 days from the administration of the prior maintenance dose.

13. The method according to claim 12, wherein the interval after the first maintenance dose for the administration of the at least one additional maintenance dose is 84 days.

14. The method according to claim 12, wherein the solvent is water.

15. The method according to claim 12, wherein the excipient is mannitol.

16. The method according to claim 12, wherein the interval after the administration of the starting dose is 28 days for the first maintenance dose.

17. The method according to claim 12, wherein the concentration of the starting dose is 40 mg of degarelix per mL of the solvent.

18. The method according to claim 12, wherein the concentration of the maintenance dose chosen from the first and the at least one additional maintenance dose ranges from 55 mg to 65 mg of degarelix per mL of the solvent.

19. The method according to claim 18, wherein the concentration of the maintenance dose chosen from the first and the at least one additional maintenance dose is 60 mg of degarelix per mL of the solvent.

20. The method according to claim 12, wherein the starting dose is 240 mg of degarelix or pharmaceutically acceptable salt thereof.

21. The method according to claim 12, wherein the maintenance dose chosen from the first and the at least one additional maintenance dose ranges from 360 mg to 480 mg of degarelix or pharmaceutically acceptable salt thereof.

22. The method according to claim 12, wherein 28 days after the administration of the starting dose, the patient exhibits a trough plasma concentration of at least 9 ng/mL.

23. The method according to claim 12, wherein after the administration of the maintenance dose chosen from the first and the at least one additional maintenance dose, the patient exhibits a trough plasma concentration of at least 9 ng/ml.

24. The method according to claim 12, wherein 3 days after the administration of the starting dose, the patient exhibits a serum testosterone level ranging from 0 ng/mL to 0.5 ng/mL.

25. The method according to claim 24, wherein after the administration of the maintenance dose chosen from the first and the at least one additional maintenance dose, the patient exhibits a serum testosterone level ranging from 0 ng/mL to 0.5 ng/mL.

26. A method of treating prostate cancer in a patient in need thereof comprising:
administering to the patient a starting dose comprising degarelix or pharmaceutically acceptable salt thereof, an excipient, and a solvent, wherein the starting dose is 240 mg of degarelix or pharmaceutically acceptable salt thereof at a concentration of 40 mg of degarelix per mL of the solvent;
administering to the patient, 28 days after the administration of the starting dose, a first maintenance dose comprising degarelix or pharmaceutically acceptable salt thereof, an excipient, and a solvent, wherein the maintenance dose is 480 mg of degarelix or pharmaceutically acceptable salt thereof at a concentration of 60 mg of degarelix per mL solvent; and
repeating, at least once, the administration of an additional maintenance dose to the patient 84 days after the administration of the prior maintenance dose.

27. The method according to claim 26, wherein 28 days after the administration of the starting dose, the patient exhibits a mean trough plasma concentration of at least 9 ng/mL.

28. The method according to claim 26, wherein after the administration of the maintenance dose chosen from the first and the at least one additional maintenance dose, the patient exhibits a mean trough plasma concentration of at least 9 ng/ml.

29. The method according to claim 26, wherein 3 days after the administration of the starting dose, the patient exhibits a serum testosterone level ranging from 0 ng/mL to 0.5 ng/mL.

30. The method according to claim 29, wherein after the administration of the maintenance dose chosen from the first and the at least one additional maintenance dose, the patient exhibits a serum testosterone level ranging from 0 ng/mL to 0.5 ng/mL.

31. A method of treating prostate cancer in a patient in need thereof comprising:
   administering to the patient a starting dose comprising degarelix or pharmaceutically acceptable salt thereof, an excipient, and a solvent, wherein the starting dose is 240 mg of degarelix or pharmaceutically acceptable salt thereof at a concentration of 40 mg of degarelix per mL of the solvent;
   administering to the patient, 28 days after the administration of the starting dose, a first maintenance dose comprising degarelix or pharmaceutically acceptable salt thereof, an excipient, and a solvent, wherein the maintenance dose is 360 mg of degarelix or pharmaceutically acceptable salt thereof at a concentration of 60 mg of degarelix per mL solvent; and
   repeating, at least once, the administration of an additional maintenance dose to the patient 84 days after the administration of the prior maintenance dose.

32. The method according to claim 31, wherein 28 days after the administration of the starting dose, the patient exhibits a mean trough plasma concentration of at least 9 ng/mL.

33. The method according to claim 31, wherein after the administration of the maintenance dose chosen from the first and the at least one additional maintenance dose, the patient exhibits a mean trough plasma concentration of at least 9 ng/ml.

34. The method according to claim 31, wherein 3 days after the administration of the starting dose, the patient exhibits a serum testosterone level ranging from 0 ng/mL to 0.5 ng/mL.

35. The method according to claim 34, wherein after the administration of the maintenance dose chosen from the first and the at least one additional maintenance dose, the patient exhibits a serum testosterone level ranging from 0 ng/mL to 0.5 ng/mL.

* * * * *

UNITED STATES PATENT AND TRADEMARK OFFICE
CERTIFICATE OF CORRECTION

PATENT NO. : 8,722,088 B2  
APPLICATION NO. : 12/771199  
DATED : May 13, 2014  
INVENTOR(S) : Olesen et al.

Page 1 of 1

It is certified that error appears in the above-identified patent and that said Letters Patent is hereby corrected as shown below:

In the Claims

Claim 1, Col. 16, Line 35, "60 g" should read as --60mg--.

Signed and Sealed this  
Fifth Day of August, 2014

Michelle K. Lee  
*Deputy Director of the United States Patent and Trademark Office*